(12) United States Patent
Shin et al.

(10) Patent No.: US 12,325,712 B2
(45) Date of Patent: Jun. 10, 2025

(54) METHOD FOR PREPARING NALDEMEDINE

(71) Applicant: YONSUNG FINE CHEMICAL CO., LTD., Hwaseong-si (KR)

(72) Inventors: Hyunik Shin, Suwon-si (KR); Hyoseon Lee, Bucheon-si (KR)

(73) Assignee: YONSUNG FINE CHEMICAL CO., LTD., Hwaseong-si (KR)

(*) Notice: Subject to any disclaimer, the term of this patent is extended or adjusted under 35 U.S.C. 154(b) by 819 days.

(21) Appl. No.: 17/604,605

(22) PCT Filed: Apr. 14, 2020

(86) PCT No.: PCT/KR2020/005007
§ 371 (c)(1),
(2) Date: Oct. 18, 2021

(87) PCT Pub. No.: WO2020/213911
PCT Pub. Date: Oct. 22, 2020

(65) Prior Publication Data
US 2022/0194953 A1 Jun. 23, 2022

(30) Foreign Application Priority Data
Apr. 19, 2019 (KR) .................. 10-2019-0046088

(51) Int. Cl.
*C07D 489/08* (2006.01)
(52) U.S. Cl.
CPC ................. *C07D 489/08* (2013.01)
(58) Field of Classification Search
CPC .................................... C07D 489/08
USPC ........................................... 546/45
See application file for complete search history.

(56) References Cited

U.S. PATENT DOCUMENTS 8,084,460 B2    12/2011  Inagaki et al.
9,951,082 B2 *  4/2018   Inagaki .................. A61P 1/14

FOREIGN PATENT DOCUMENTS

| | | |
|---|---|---|
| CN | 105985348 A | 10/2016 |
| JP | 2003-528819 A | 9/2003 |
| KR | 10-2008-0014791 A | 2/2008 |
| KR | 10-2009-0057031 A | 6/2009 |
| KR | 10-2014-0057410 A | 5/2014 |
| WO | 2006/126529 A1 | 11/2006 |
| WO | 2012/063933 A1 | 5/2012 |

OTHER PUBLICATIONS

Hideaki Fujii et al., "The First Example of the Stereoselective Synthesis of 7β-Carbamoyl-4,5α-epoxymorphinan via a Novel and Reactive γ-Lactone", Chem. Pharm. Bull., Jun. 2004, pp. 747-750, vol. 52, No. 6.
International Search Report for PCT/KR2020/005007, dated Sep. 8, 2020.
European Patent Office, Search Report issued Jan. 11, 2023 in European Application No. 20 79 2080.
Inagaki et al., "Discovery of naldemedine: A potent and orally available opioid receptor antagonist for treatment of opioid-induced adverse effects", Bioorganic & Medicinal Chemistry Letters 29 (2019) 73-77.

* cited by examiner

*Primary Examiner* — Niloofar Rahmani
(74) *Attorney, Agent, or Firm* — Sughrue Mion, PLLC

(57) ABSTRACT

Provided is a cost-effective process for preparing naldemedine having high purity with high yields.

14 Claims, No Drawings

METHOD FOR PREPARING NALDEMEDINE

CROSS REFERENCE TO RELATED APPLICATIONS

This is a National Stage of International Application No. PCT/KR2020/005007 filed Apr. 14, 2020, claiming priority based on Korean Patent Application No. 10-2019-0046088 filed Apr. 19, 2019, the contents of all of which are incorporated herein by reference in their entirety.

TECHNICAL FIELD

The present invention relates to a process for preparing naldemedine. More particularly, the present invention relates to a cost-effective process for preparing naldemedine having high purity with high yields.

BACKGROUND ART

Opioid analgesics act on μ-opioid receptors in the brain, leading to a strong analgesic action. Also, they act on μ-opioid receptors in the intestinal tract as well, thereby lowering intestinal activity and causing severe constipation symptoms.

Naldemedine represented by the following formula (1) is a peripherally acting μ-opioid receptor antagonist, which is a medication approved for the treatment of opioid-induced constipation in adults.

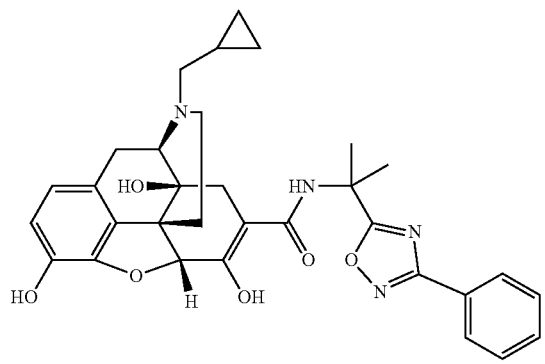

(1)

Naldemedine relieves constipation symptoms by binding to the peripheral μ-opioid receptor to antagonize the action of the opioid analgesic without weakening the analgesic action of opioid analgesics.

U.S. Pat. No. 8,084,460 discloses a process for preparing naldemedine by total six steps of protection of naltrexone with a benzyl group, ethoxycarbonylation, protection with a benzyl group, hydrolysis, coupling, and deprotection, as shown in the following reaction scheme 1. However, the above process has problems of expensive reagents, severe reaction conditions, and low yields, so that it is not suitable for mass production.

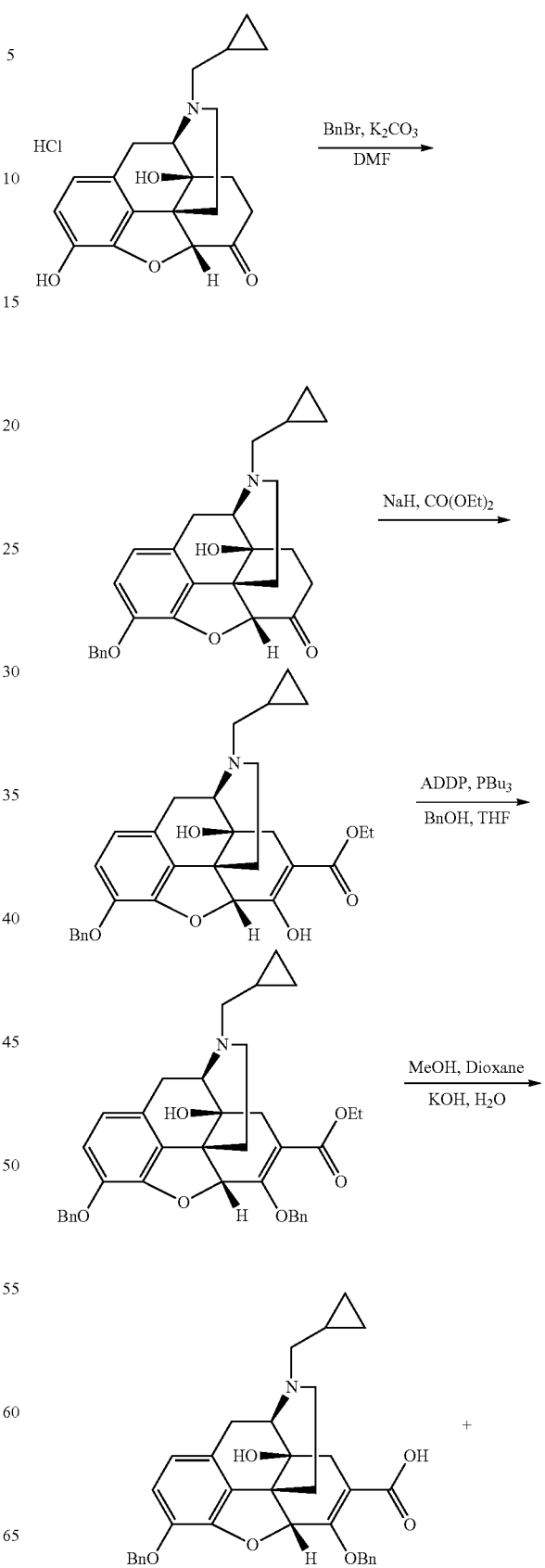

[Reaction Scheme 1]

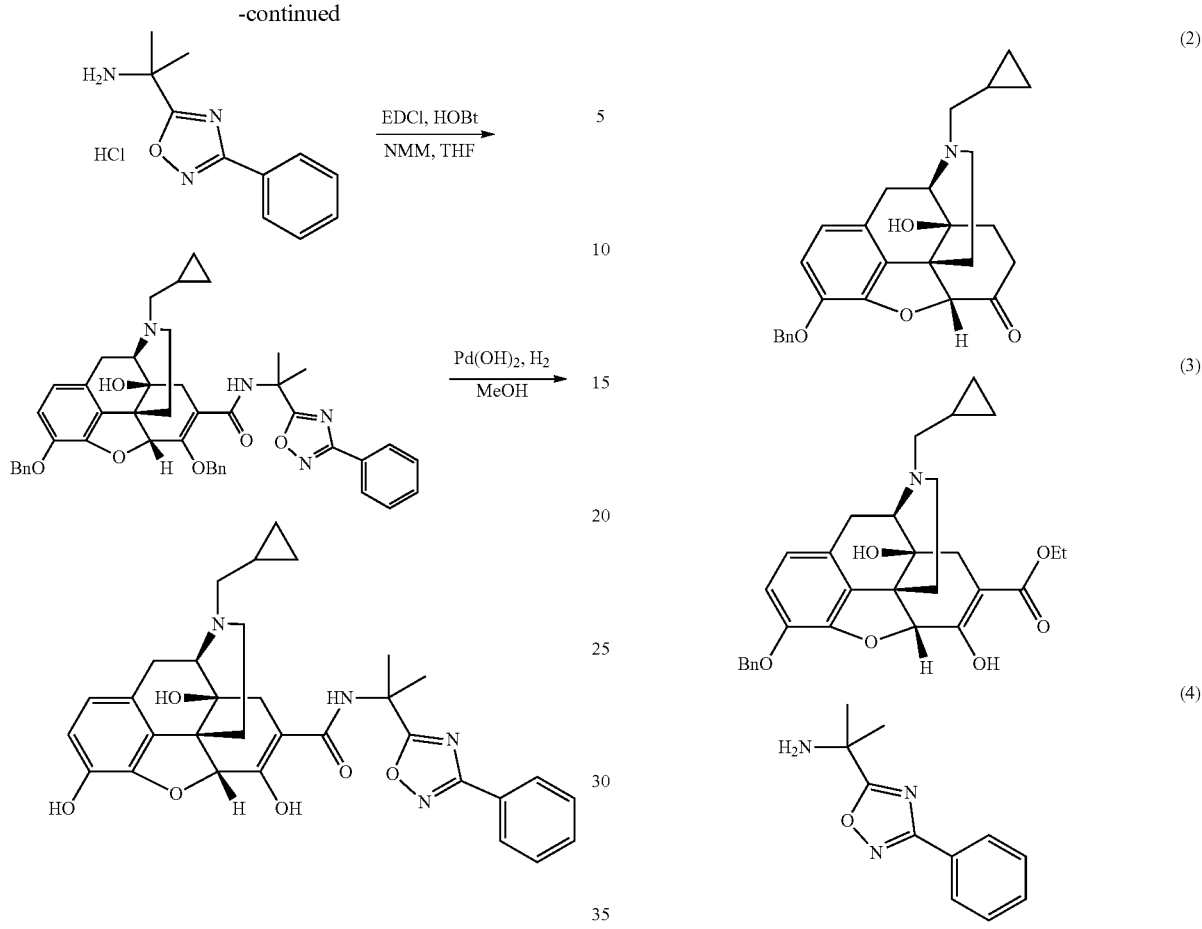

DISCLOSURE

Technical Problem

An object of the present invention is to provide a cost-effective process for preparing naldemedine with high yields.

Another object of the present invention is to provide a process for preparing naldemedine having high purity only by recrystallization without a purification process using column chromatography.

Technical Solution

One embodiment of the present invention relates to a process for preparing naldemedine of the following formula (1), comprising the steps of:

(i) reacting a compound of the following formula (2) with diethyl pyrocarbonate, followed by treating with a base to obtain a compound of the following formula (3);

(ii) subjecting the compound of the following formula (3) to a combination reaction with a compound of the following formula (4), followed by adding hydrochloric acid to obtain a compound of the following formula (5); and (iii) deprotecting the compound of the following formula (5).

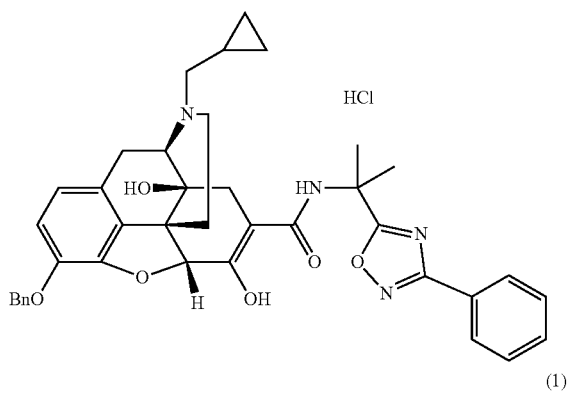

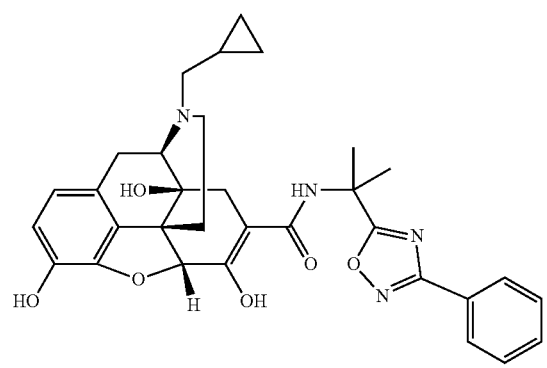

Hereinafter, the preparation process of the present invention is described in more detail referring to the following reaction scheme 2. The process depicted in the following reaction scheme 2 represents merely a typical example, and various changes may be made to reagents and reaction conditions without limitation.

[Reaction Scheme 2]

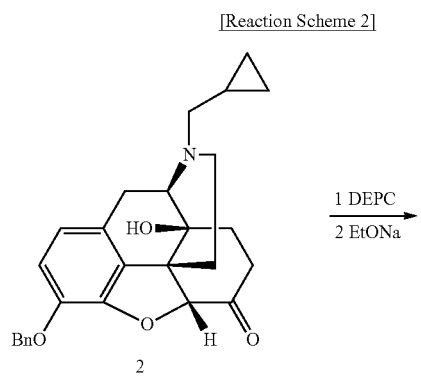
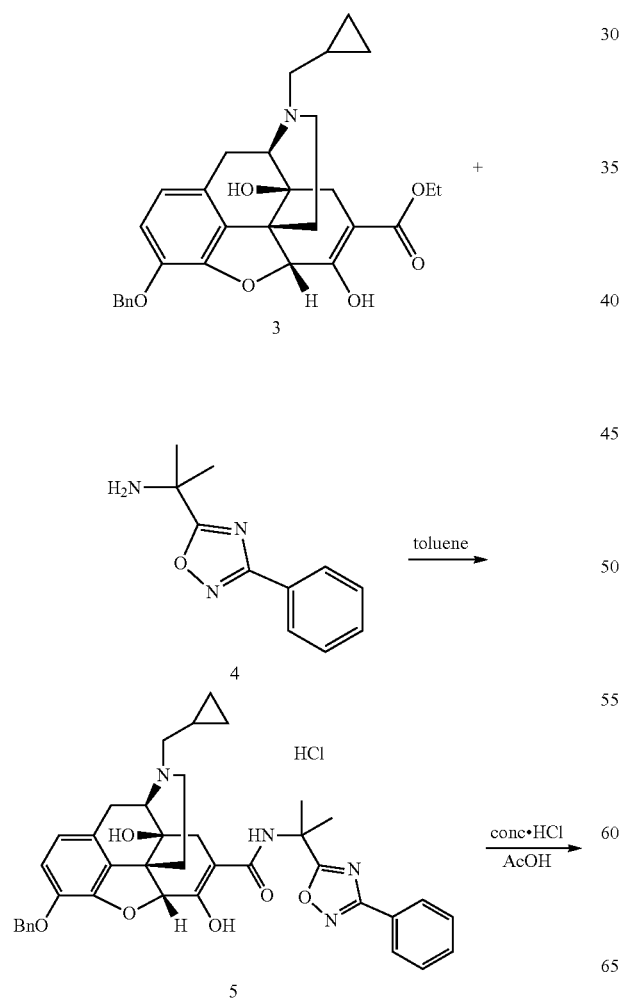
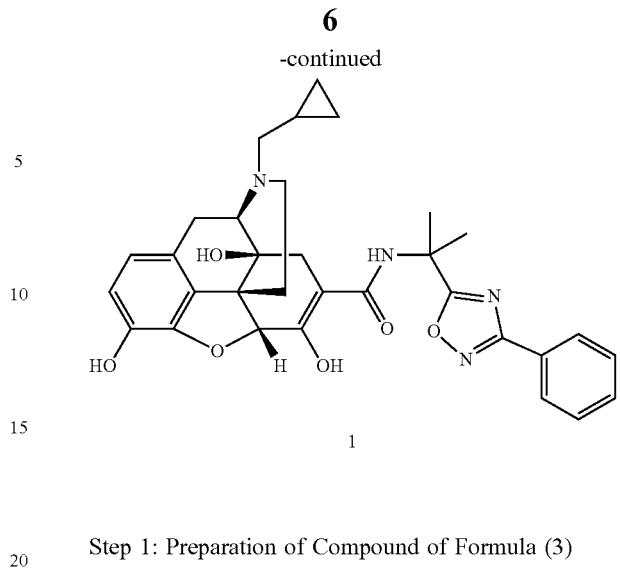

Step 1: Preparation of Compound of Formula (3)

The compound of formula (3) can be obtained by reacting the compound of formula (2) with diethyl pyrocarbonate and then treating with a base.

As shown in the following reaction scheme 3, when the compound of formula (2) is reacted with diethyl pyrocarbonate (DEPC), the hydroxyl group of the compound of formula (2) is ethoxycarbonylated to give a carbonate intermediate, and when the intermediate is treated with a base, the ethoxycarbonyl group is transferred to the α-position of the ketone group to give the compound of formula (3).

[Reaction Scheme 3]

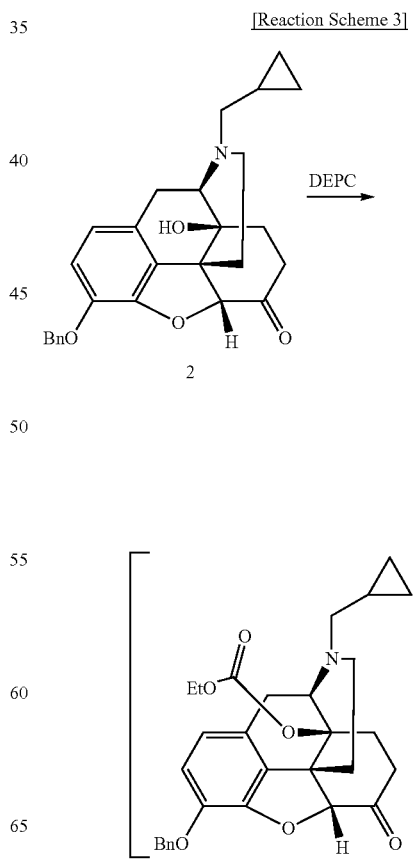

-continued

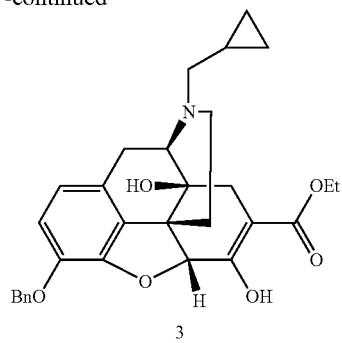

As the base, sodium ethoxide, potassium ethoxide, lithium ethoxide, etc. may be used. Particularly, sodium ethoxide is preferred.

The reaction with diethyl pyrocarbonate is preferably performed at about 100 to 120° C., and the base treatment is preferably performed at room temperature.

The obtained compound of formula (3) may be purified by recrystallization. As the recrystallization solvent, a mixed solvent of ethyl acetate and methanol is preferred.

In one aspect of the present invention, the compound of formula (2) may be synthesized by protecting a compound of the following formula (6) with a benzyl group.

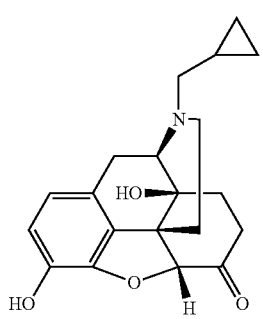

(6)

The protection may be carried out by reacting the compound of formula (6) with benzyl bromide in the presence of a base.

As the base, potassium carbonate, cesium carbonate, sodium hydride, sodium hydroxide, etc. may be used. Particularly, potassium carbonate in the form of a fine powder is preferred.

The reaction temperature is preferably about 50 to 70° C.

As the reaction solvent, acetone, dimethylformamide, etc. may be used. Particularly, acetone is preferred in terms of a work-up process and yield.

Step 2: Preparation of Compound of Formula (5)

The compound of formula (5) can be obtained by subjecting the compound of formula (3) to a combination reaction with the compound of formula (4) and then adding hydrochloric acid thereto.

The combination reaction may be carried out in the absence of a separate reaction reagent such as a catalyst.

As the reaction temperature, heating under reflux condition is preferred. The reaction time is preferably 3 to 4 days.

As the reaction solvent, toluene, benzene, xylene, etc. may be used. Particularly, toluene is preferred.

The obtained compound of formula (5) may be purified by recrystallization. As the recrystallization solvent, ethyl acetate is preferred.

Step 3: Preparation of Naldemedine of Formula (1)

The compound of formula (1) can be obtained by deprotecting the compound of formula (5).

The deprotection may be carried out using concentrated hydrochloric acid in acetic acid.

The reaction temperature is preferably about 50 to 60° C.

The obtained naldemedine of formula (1) can be solidified by adding it to aqueous ammonia at 0° C.

The naldemedine prepared by the above process can be used for the preparation of an acid addition salt of naldemedine by adding an acid thereto, without additional purification process.

As the acid, p-toluenesulfonic acid, acetic acid, hydrochloric acid, etc. may be used. Particularly, p-toluenesulfonic acid is preferred.

The acid addition reaction is preferably performed at room temperature. As the reaction solvent, methanol and the like may be used.

The prepared p-toluenesulfonic acid salt of naldemedine can be purified by recrystallization. As the recrystallization solvent, methylene chloride is preferred.

One embodiment of the present invention relates to a compound of the following formula (5) which is an intermediate for preparing naldemedine of formula (1).

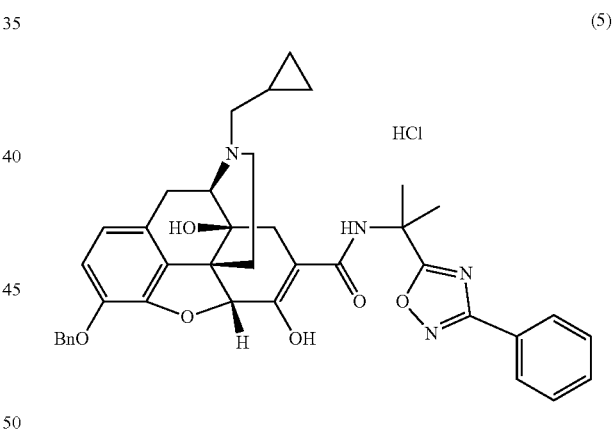

(5)

Advantageous Effects

In accordance with the preparation process of the present invention, naldemedine can be cost-effectively, efficiently, and simply prepared. Further, naldemedine having high purity can be prepared with high yields only by recrystallization without a purification process using column chromatography. Therefore, it is suitable for mass production.

BEST MODE

Hereinafter, the present invention will be described in more detail by the following examples. It will be obvious to those skilled in the art that these examples are merely described for illustration of the present invention and the scope of the present invention is not limited thereto.

Preparation Example 1: Synthesis of Compound of Formula (4)

t-Butoxycarbonylamino isobutyric acid (200 g, 1.0 equiv) was added to n-propyl acetate (1400 mL, 7 vol.) followed by stirring, and then N,N-diisopropylethylamine (DIPEA, 188.5 mL, 1.1 equiv) was added thereto at 0° C. Then, isobutyl chloroformate (IBCF, 134.7 mL, 1.05 equiv) was added dropwise thereto at 0° C., and the resulting mixture was stirred for 1 hour. A solution of benzamide oxime (140.7 g, 1.05 equiv) in n-propyl acetate (800 mL, 4 vol.) was added and stirred at 0° C. for 1 hour. Then, the resulting mixture was heated at 95° C. for 5 hours. After confirming that the reaction was completed with TLC ($CH_2Cl_2$:MeOH=20:1), the reaction product was quenched with 0.1 N HCl solution (3000 mL, 10 vol.), and the organic phase was washed with saturated $NaHCO_3$ solution (3000 mL, 10 vol.) and water (3000 mL, 10 vol.). After drying over $Na_2SO_4$ and concentration, the residue (300 g) was diluted with 4 N HCl in dioxane (3000 mL, 10 vol), and stirred at 20° C. for 2 hours. After filtration of the resulting white solid, the filter cake was washed with methyl t-butyl ether (MTBE, 300 mL, 1 vol.). The filtrate was evaporated, and MTBE (500 mL, 10 vol.) was added and stirred, followed by filtration. The filter cake was washed with MTBE (50 mL, 1 vol.). The filter cakes were combined and dried in a vacuum oven to give the HCl salt of the compound of formula (4) (228 g, 97.6% yield) as a white solid. Then, saturated sodium hydrogen carbonate solution (2 L) and MTBE (2 L) were added thereto and strongly stirred for 30 minutes, and then the organic layer was separated, followed by concentration. The obtained solid was dried in a vacuum oven to obtain the compound of formula (4) (190 g, 98% yield) as a white solid.

$^1$H NMR (300 MHz, DMSO): 9.16 (3H, s), 8.05-8.02 (2H, m), 7.65-7.59 (3H, m), 1.79 (6H, s).

m/z [M+H]=204.1

Preparation Example 2: Synthesis of Compound of Formula (2)

The compound of formula (6) (100 g, 1 equiv), BnBr (41 mL, 1.3 equiv) and $K_2CO_3$ (110 g, 3 equiv) were added to acetone (1000 mL, 10 vol.) and stirred, followed by heating at 60° C. for 20 hours. After confirming that the reaction was completed with TLC ($CH_2Cl_2$:MeOH=15:1), the reaction product was cooled to room temperature and filtered. Then, the filter cake was washed with acetone (200 mL×2, 2 vol.). The filtrate was evaporated, and the residue was diluted with 2N HCl solution (300 mL, 3 vol.) and washed with MTBE (300 mL×2, 3 vol.). After that, it was neutralized with $NH_3·H_2O$ and extracted with $CH_2Cl_2$ (300 mL×2, 3 vol.). The organic phases were combined and dried over $Na_2SO_4$, followed by evaporation to obtain the compound of formula (2) (106.93 g, 93.6% yield) as a pale yellow gum.

$^1$H NMR (300 MHz, $CDCl_3$): 7.47-7.44 (2H, m), 7.37-7.25 (3H, m), 6.72-6.54 (2H, dd, J=8.1 Hz), 5.31-5.18 (3H, m), 4.68 (1H, s), 3.18-3.16 (1H, d), 3.06-3.00 (2H, m), 2.76-2.12 (7H, m), 1.96-1.83 (1H, m), 1.64-1.53 (2H, m), 0.98-0.77 (1H, m), 0.57-0.53 (2H, m), 0.15-0.13 (2H, m);

$^{13}$C NMR (300 MHz, $CDCl_3$): δ=208.5, 145.5, 141.8, 137.5, 129.8, 128.3, 127.7, 125.6, 119.4, 118.0, 90.4, 72.1, 70.1, 62.0, 59.2, 50.7, 43.5, 36.2, 31.5, 30.7, 22.6, 9.4, 3.9, 3.8.

m/z [M+H]=432.2

Example 1: Synthesis of Compound of Formula (3)

A stirred mixture of the compound of formula (2) (106.9 g, 1 equiv) and diethyl pyrocarbonate (DEPC, 1000 mL, 10 vol.) was heated at 110° C. for 20 hours. The volatiles were evaporated, and the residue was diluted with EtOH (1000 mL, 10 vol.). To the resulting mixture was added dropwise EtONa (107 mL, 1 vol., 20% solution in EtOH), and the mixture was stirred at 20° C. for 1 hour. After confirming that the reaction was completed with TLC ($CH_2Cl_2$:MeOH=15:1), the reaction mixture was neutralized with 1 N HCl solution at 0° C. The resulting mixture was concentrated and the residue was diluted with $CH_2C_2$ (1000 mL, 10 vol.) and water (500 mL, 5 vol.). The organic layer was separated, and the separated aqueous layer was extracted with $CH_2Cl_2$ (300 mL). The organic layers were combined and dried over $Na_2SO_4$, followed by concentration. The crude product was purified by crystallization (EA:MeOH=2 vol.:4 vol.) and filtered. The filter cake was washed with MeOH (1 vol.). The filtrate was evaporated and recrystallized again. The two filter cakes were combined and dried in a vacuum oven to obtain the compound of formula (3) (110 g, 88% yield, 98.4% purity) as a white solid.

$^1$H NMR (300 MHz, $CDCl_3$): 12.06 (1H, s), 7.43-7.39 (2H, m), 7.34-7.25 (3H, m), 6.74-6.54 (2H, dd, J=8.1 Hz), 5.20-5.18 (2H, t, J=4.2 Hz), 4.95 (1H, s), 4.89 (1H, br), 4.17-4.14 (2H, m), 3.23-3.21 (1H, d), 3.09-3.03 (1H, d), 2.69-2.25 (7H, m), 2.03-1.98 (1H, d), 1.75-1.65 (2H, d), 1.28-1.23 (3H, t, J=6.9), 0.97-0.77 (1H, m), 0.57-0.54 (2H, m), 0.15-0.12 (2H, m);

$^{13}$C NMR (300 MHz, $CDCl_3$): δ=172.1, 164.4, 145.3, 141.9, 137.3, 131.0, 128.3, 127.8, 126.2, 119.0, 117.7, 98.4, 87.0, 71.9, 70.0, 61.2, 60.9, 59.4, 46.5, 43.3, 31.1, 29.9, 22.9, 14.1, 9.3, 4.1, 3.6.

m/z [M+H]=504.2

Example 2: Synthesis of Compound of Formula (5)

The compound of formula (3) (100 g, 1 equiv) and the compound of formula (4) (60.54 g, 1.5 equiv) were added to toluene (200 mL, 2 vol.), followed by stirring and then heating at 110° C. for 4 days. After confirming that the reaction was completed with TLC ($CH_2Cl_2$:MeOH=15:1), the reaction mixture was diluted with $CH_2Cl_2$ (1000 mL, 10 vol.), and washed with 0.1 N HCl solution (500 mL×5, 5 vol.), saturated $NaHCO_3$ solution (500 mL, 5 vol.) and brine (500 mL, 5 vol.). The separated organic layer was dried over $Na_2SO_4$ and concentrated. The crude product (65 g) was diluted with EA (688 mL, 7.5 vol.) and 4 N HCl solution (26 mL, 1.05 equiv) in dioxane was added dropwise thereto. After dropwise addition, the mixture was heated under reflux to give a clear solution. The clear solution was slowly cooled to room temperature. The formed solid was filtered, and the filter cake was washed with EA (32 mL, 0.5 vol.) and MTBE (65 mL, 1 vol.). The filter cake was dried in a vacuum oven to obtain the compound of formula (5) (47 g, 73% yield, 99.5% purity) as a white solid.

$^1$H NMR (300 MHz, DMSO): 13.30 (1H, s), 8.23 (1H, br), 8.00 (1H, s), 7.99-7.97 (2H, m), 7.59-7.53 (3H, m), 7.41-7.28 (5H, m), 6.96-6.73 (2H, dd, J=8.1 Hz), 5.17-5.12 (2H, m), 5.04 (1H, s), 4.04-4.02 (1H, d), 3.47-2.04 (9H, m), 1.72-1.70 (6H, d), 1.66-1.60 (1H, d), 1.17-1.06 (1H, m), 0.75-0.61 (2H, m), 0.55-0.39 (2H, m);

$^{13}$C NMR (300 MHz, DMSO): δ=183.4, 171.4, 167.8, 161.4, 145.1, 142.1, 137.2, 132.0, 129.7, 129.6, 128.8, 128.7, 128.3, 127.4, 126.6, 124.1, 120.3, 117.4, 98.4, 86.5, 70.8, 70.0, 60.4, 57.2, 52.1, 45.9, 45.0, 30.9, 28.0, 26.7, 26.5, 24.0, 6.1, 5.7, 2.8.

m/z [M+H]=661.3

Example 3: Synthesis of Naldemedine of Formula (1)

The compound of formula (5) (10 g, 1 equiv) and conc. HCl (20 mL, 2 vol.) were added to acetic acid (40 mL, 4 vol.) and stirred, followed by heating at 60° C. for 3 hours. After confirming that the reaction was completed with TLC (CH$_2$Cl$_2$:MeOH=15:1), the reaction mixture was cooled to room temperature and added dropwise to a mixture of NH$_3$·H$_2$O (75 mL, 7.5 vol.) and water (75 mL, 7.5 vol.) at 0° C. The precipitated white solid was filtered, and then the filter cake was washed with water (20 mL×2, 2 vol.). The separated solid was diluted with EtOAc (80 mL, 8 vol.), and dried over Na$_2$SO$_4$, followed by concentration. MTBE (10 mL, 10 vol.) was added to the residue and stirred to solidify the product, followed by filtration. The product was used in the next step without additional purification.

$^1$H NMR (300 MHz, DMSO): 13.40 (1H, br), 9.16 (1H, br), 8.08 (1H, br), 7.99-7.95 (2H, m), 7.58-7.52 (3H, m), 6.60-6.53 (2H, m), 4.77 (1H, br), 4.72 (1H, s), 3.33-1.97 (8H, m), 1.69-1.58 (6H, m), 1.43-1.14 (2H, m), 0.88-0.81 (1H, m), 0.53-0.47 (2H, m), 0.15-0.14 (2H, m).

m/z [M+H]=571.2

Example 4: Synthesis of Naldemedine Tosylate

To a solution of the compound of formula (1) (6.5 g, 1 equiv) in MeOH (65 mL, 10 vol.) was added p-toluenesulfonic acid (PTSA, 2.1 g, 1 equiv), followed by stirring at 20° C. for 16 hours. Then, the resulting mixture was evaporated, and ACN and MTBE (ACN:MTBE=1:10) were added to the residue and stirred, followed by filtration. The filter cake was washed with MTBE (1 vol.). Then, it was diluted with MC (10 vol.) and stirred for 2 days. The resulting white solid was crystallized (unsolvated) (99.8% purity).

The invention claimed is:

1. A process for preparing naldemedine of the following formula (1), which comprises the steps of:
   (i) reacting a compound of the following formula (2) with diethyl pyrocarbonate, followed by treating with a base to obtain a compound of the following formula (3);
   (ii) subjecting the compound of the following formula (3) to a combination reaction with a compound of the following formula (4), followed by adding hydrochloric acid to obtain a compound of the following formula (5); and
   (iii) deprotecting the compound of the following formula (5):

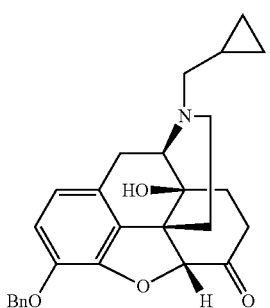

(2)

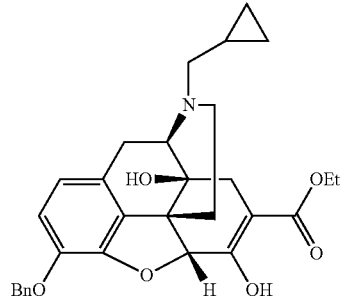

(3)

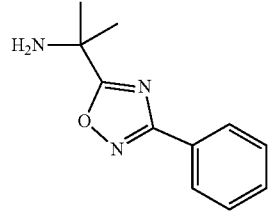

(4)

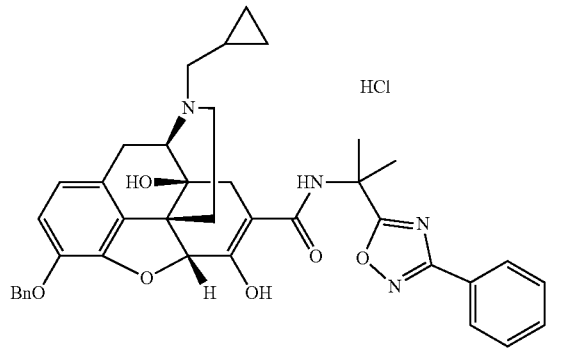

(5)

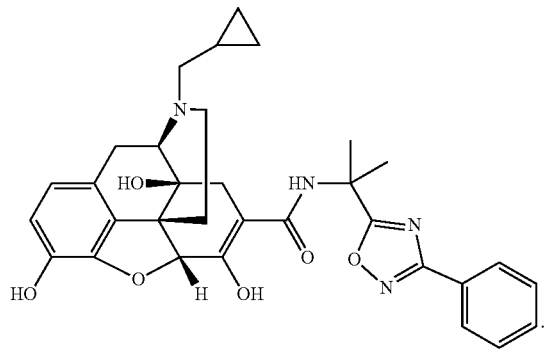

(1)

2. The process according to claim 1, wherein the base of the step (i) is sodium ethoxide.

3. The process according to claim 1, further comprising the step of purifying the compound of formula (3) obtained from the step (i) by recrystallization.

4. The process according to claim 1, wherein the compound of formula (2) is synthesized by protecting a compound of the following formula (6) with a benzyl group:

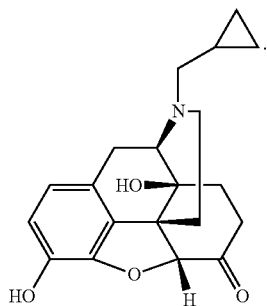

(6)

5. The process according to claim 4, wherein the protection is carried out by reacting the compound of formula (6) with benzyl bromide in the presence of a base.

6. The process according to claim 5, wherein the base is potassium carbonate in the form of a fine powder.

7. The process according to claim 5, wherein a solvent in the protection is acetone.

8. The process according to claim 1, wherein the combination reaction of the step (ii) is carried out in the absence of a separate reaction reagent.

9. The process according to claim 1, wherein the combination reaction of the step (ii) is carried out under a heating under reflux condition, and a solvent in the combination reaction is toluene.

10. The process according to claim 1, further comprising the step of purifying the compound of formula (5) obtained from the step (ii) by recrystallization.

11. The process according to claim 1, wherein the deprotection of the step (iii) is carried out using concentrated hydrochloric acid in acetic acid.

12. A process for preparing an acid addition salt of naldemedine, which comprises the step of adding an acid to the naldemedine prepared by the process according to claim 1.

13. The process according to claim 12, wherein the acid is p-toluenesulfonic acid, acetic acid, or hydrochloric acid.

14. The process according to claim 12, wherein the acid addition salt is a p-toluenesulfonic acid salt.

* * * * *